United States Patent [19]

Callens et al.

[11] Patent Number: 5,506,362

[45] Date of Patent: Apr. 9, 1996

[54] PROCESS FOR THE PREPARATION OF AN α-AMINO ACID AMIDE

[75] Inventors: Roland Callens, Drongen; Georges Blondeel, Aalst, both of Belgium

[73] Assignee: Solvay (Société Anonyme), Brussels, Belgium

[21] Appl. No.: 257,293

[22] Filed: Jun. 9, 1994

[30] Foreign Application Priority Data

Jun. 18, 1993 [BE] Belgium ............................. 09300622

[51] Int. Cl.$^6$ ..................... C07D 209/20; C07D 233/64; C07C 231/02
[52] U.S. Cl. ................. 548/497; 548/496; 548/339.1; 564/138; 564/139; 564/140; 564/141; 530/324
[58] Field of Search ..................... 548/496, 497, 548/339.1; 564/138, 139, 140, 141; 530/324

[56] References Cited

U.S. PATENT DOCUMENTS 5,158,962  10/1992  Seitz et al. .......................... 514/335

FOREIGN PATENT DOCUMENTS

| | | |
|---|---|---|
| 0401817 | 12/1990 | European Pat. Off. |
| 0425925 | 5/1991 | European Pat. Off. |
| 0477639 | 4/1992 | European Pat. Off. |
| 0562659 | 9/1993 | European Pat. Off. |
| 3339308 | 10/1983 | Germany. |
| 917518 | 9/1991 | South Africa. |

OTHER PUBLICATIONS

Von Th. Wieland et al "Über Peptidsynthesen, 32. Mitt." In: Die Makromolekulare Chemie, vol. 92, 1966, pp. 277–286.
R. A. Boissonnas et al. "Etude comparative de la scission de divers groupes de blocage de la fonction α–amino des acides aminés". In: Helv. Chim. Acta, vol. 36, No. 4, 1953 pp. 875–886.

*Primary Examiner*—David B. Springer
*Attorney, Agent, or Firm*—Spencer, Frank & Schneider

[57] ABSTRACT

An α-amino acid amide is prepared by reaction of an $N^\alpha$-aryloxycarbonylamino acid with a compound containing a free amino group. This process makes it possible readily to prepare peptides, by direct reaction between the carboxyl group of the $N^\alpha$-aryloxycarbonyl derivative of an amino acid and the free amino group of a second amino acid or of a peptide fragment, without requiring protection of the carboxyl function of the second amino acid or of the peptide fragment, nor a coupling agent nor a deprotection step.

12 Claims, No Drawings

PROCESS FOR THE PREPARATION OF AN α-AMINO ACID AMIDE

The present invention relates to a new process for the preparation of an α-amino acid amide which may be used in particular in peptide synthesis.

According to a conventional route, a synthetic peptide may be prepared in solution by addition (condensation) of an amino acid, the amino group of which is protected and the carboxyl group of which is activated, to a peptide chain or to another amino acid in the case of the preparation of a dipeptide. However, such a process involves a large number of steps. Thus, in order to prepare a dipeptide from two single amino acids having no reactive groups on their side chain, it requires, prior to the condensation reaction, the amino group of the first amino acid and the carboxyl group of the second amino acid to be protected and the carboxyl group of the first amino acid to be activated and then, after the condensation reaction between the activated carboxyl group of the first amino acid and the free amino group of the second amino acid, it also involves a deprotection of the amino group of the first amino acid constituting the dipeptide and of the carboxyl group of the second amino acid constituting the dipeptide. The overall chemical yield for the synthesis is, of course, affected by the large number of synthesis steps, and even more so when a chirally pure product is desired.

The invention redresses the disadvantages of the conventional processes for peptide synthesis in solution by providing a new process for coupling an α-amino acid with a compound containing a free amino group, the process requiring a limited number of steps and making it possible to obtain the desired product with an improved chemical yield, while notably conserving the chiral purity of the structures used.

Consequently, the invention relates to a process for the preparation of an α-amino acid amide, according to which a compound containing a free amino group is reacted, in basic medium, with a derivative of the amino acid containing an $N^\alpha$-aryloxycarbonyl group. This process is particularly advantageous in peptide synthesis.

Amino acid is understood to denote, for the purposes of the present invention, any compound containing at least one amino group and at least one carboxyl group. By extension, the term "amino acid" is also understood below to encompass any amino acid as defined above in which certain other groups are possibly linked to organic groups such as protecting groups. In particular, α-amino acid is understood to denote any amino acid in which at least one amino group and at least one carboxyl group are linked to the same carbon atom of the molecule. This may in particular be alanine, valine, leucine, isoleucine, proline, phenylalanine, tryptophan, methionine, glycine, serine, threonine, cysteine, arginine, tyrosine, asparagine, glutamine, lysine, histidine, glutamic acid and aspartic acid.

Amino acid derivative containing an $N^\alpha$-aryloxycarbonyl group, also referred to hereinafter as $N^\alpha$-aryloxycarbonylamino acid, is understood to denote any α-amino acid derivative in which an aryloxycarbonyl group of formula R—O—CO—, with R symbolizing an aryl group, is linked to the nitrogen atom of an α-amino group of the amino acid.

Peptide is understood to denote, for the purposes of the present invention, any compound consisting of the combination of at least two amino acids as defined above, in which at least one bond between two amino acids is a normal peptide bond, that is to say an amide bond between an α-amino group of an amino acid and a carboxyl group of another amino acid.

In the process according to the invention, the use of an $N^\alpha$-aryloxycarbonylamino acid is essential. Indeed it appeared, surprisingly, that the aryloxycarbonyl group linked to the α-amino group of the amino acid induces, in the presence of a compound containing a free amino group, a reaction of the free carboxyl group of the said amino acid with the free amino group of the said compound and that the amino group of the amino acid is concomitantly freed of the aryloxycarbonyl group which was bonded thereto. The process according to the invention thus makes it possible to obtain readily an α-amino acid amide free of $N^\alpha$-aryloxycarbonyl group.

The $N^\alpha$-aryloxycarbonyl derivative of the amino acid used generally includes a group containing from 7 to 15 carbon atoms as aryloxycarbonyl group. This aryloxycarbonyl group is most often a phenyloxycarbonyl or naphthyloxycarbonyl group, optionally substituted with at least one group chosen from alkyl groups containing 1 to 4 carbon atoms and nitro, halo and haloalkyl groups. By way of examples of aryloxycarbonyl groups which may be used in the process of the invention, there may be mentioned phenyloxycarbonyl, tolyloxycarbenyl, xylyloxycarbonyl, mesitylyloxycarbonyl, ethylphenyloxycarbonyl, diethylphenyloxycarbonyl, propylphenyloxycarbonyl, isopropylphenyloxycarbonyl, nitrophenyloxycarbonyl, dinitrophenyloxycarbonyl, chlorophenyloxycarbonyl, trichloromethylphenyloxycarbonyl, trifluoromethylphenyloxycarbonyl and naphthyloxycarbonyl groups. The aryloxycarbonyl group is preferably a phenyloxycarbonyl, tolyloxycarbonyl, p-nitrophenyloxycarbonyl, 2,4-dinitrophenyloxycarbonyl, p-chlorophenyloxycarbonyl or p-trichloromethylphenyloxycarbonyl group. Good results were obtained in the process according to the invention with the $N^\alpha$-phenyloxycarbonyl derivative of the amino acid.

An $N^\alpha$-aryloxycarbonyl derivative of any α-amino acid may be used in the process according to the invention.

The $N^\alpha$-aryloxycarbonylamino acid is a readily accessible and inexpensive product. It may conventionally be prepared by an acylation method similar to those used in order to attach a protecting group of the alkyloxycarbonyl or aralkyloxycarbonyl type to an amino group of an amino acid. A standard method, known as the Schotten-Baumann procedure, consists in reacting, in aqueous medium, the sodium form of the amino acid with a suitable acylating agent, such as an aryl chloroformate or an aryloxycarbonyloxysuccinimide.

Another procedure for the preparation of the $N^\alpha$-aryloxycarbonylamino acid, which led to excellent results and which is consequently preferred, consists in using the amino acid in the form of its persilylated derivative. This persilylated derivative may be obtained, for example, by a treatment at reflux with an excess of trimethylcyanosilane, until a homogeneous solution is obtained. This solution is subsequently diluted, for example using methylene chloride, and cooled to a temperature lower than $-10°$ C., preferably lower than or equal to $-15°$ C. The stoichiometric amount of aryl chloroformate is then added very slowly and, after reaction for a few minutes, the solution is then concentrated and the $N^\alpha$-aryloxycarbonylamino acid is isolated by the most suitable route, depending on its physicochemical properties.

The process makes it possible to prepare primary, secondary or tertiary amides, depending on the nature of the compound containing the free amino group. The compound containing a free amino group which reacts with the $N^\alpha$-aryloxycarbonylamino acid in the process according to the invention is any compound of general formula R1R2NH in which R1 and R2 represent, independently of each other, hydrogen atoms or alkyl, cycloalkyl or aralkyl radicals or in which R1 and R2 together form an alicyclic radical. In this compound, the alkyl, cycloalkyl, aralkyl or alicyclic radicals may be substituted with one or more functional groups containing at least one oxygen, sulphur or nitrogen atom, in particular such as a carboxyl, hydroxyl, mercapto, indolyl or imidazolyl group. Compounds which may be used in the process according to the invention are, for example, ammonia, primary or secondary amines, amino acids and peptides. The process according to the invention is particularly advantageous when the compound containing a free amino group is an amino acid. It constitutes in this case a very simple process for the synthesis of dipeptides.

The process according to the invention is carried out in a basic medium.

The process according to the invention is generally carried out in an aqueous liquid medium preferably containing a water-miscible organic solvent, in which medium the $N^\alpha$-aryloxycarbonylamino acid and the compound containing a free amino group are at least partially soluble. Suitable organic solvents for the process according to the invention are lower alcohols, in particular such as methanol, ethanol and isopropanol, tetrahydrofuran and dimethoxyethane. Good results were obtained in a water/ethanol medium. The water/organic solvent weight ratio may vary within a wide range. It is generally at least equal to 0.1 and does not exceed 10.

The basicity of the medium may be obtained by adding a basic compound to the medium, for example by adding an inorganic base such as LiOH, NaOH or KOH or by adding an organic base which is inert under the reaction conditions, such as a tertiary amine. Good results were obtained in the presence of triethylamine. When the compound containing a free amino group is an amino acid or a peptide containing free carboxyl functions, the basic compound must be used in a sufficient amount to neutralize the carboxyl functions. When the compound containing a free amino group has a sufficiently basic character, the basicity of the medium may optionally be obtained by working with an excess of this compound relative to the stoichiometric amount required to react with the $N^\alpha$-aryloxycarbonylamino acid.

The process according to the invention may be used in a wide range of concentration of the reactants in the liquid medium. The $N^\alpha$-aryloxycarbonylamino acid is generally used at a concentration of 0.05 to 5 mol/l, preferably from 0.1 to 1 mol/l.

The molar ratio between the compound containing a free amino group and the $N^\alpha$-aryloxycarbonylamino acid is generally at least equal to 1. This ratio is preferably at least equal to 1.1. In principle, there is no upper limit to this ratio. In practice, it is generally pointless to work with a molar ratio between the compound containing a free amino group and the $N^\alpha$-aryloxycarbonylamino acid greater than 100. Most often, the molar ratio does not exceed 10. When the compound containing a free amino group is an amino acid or a peptide, the molar ratio preferably does not exceed 5.

The reaction may be carried out between room temperature and the boiling point of the organic solvent. It is advantageously carried out between 30° and 80° C. A temperature of 40° to 60° C. is very particularly preferred.

Under these conditions, the reaction time is generally less than 10 hours. Most often, the reaction is complete after a period of 1 to 4 hours.

The process according to the invention appears to be particularly advantageous compared with the known processes for the preparation of α-amino acid amides. The $N^\alpha$-aryloxycarbonyl derivative of the amino acid used in the process according to the invention may readily and cheaply be prepared from the amino acid. It may be easily isolated in pure form. It is stable and may be conserved for a long time. The process according to the invention is particularly advantageous in peptide synthesis, that is to say when the compound containing a free amino group is an amino acid or a peptide. It constitutes, in this case, a peptide synthesis process which is particularly simple, effective and very respectful of the chirality of the compounds used. In the process according to the invention, the aryloxycarbonyl group acts both as a protecting group for the α-amino group and as an activator for the condensation reaction of the carboxyl group with a free amino group of another compound. In addition, when the $N^\alpha$-aryloxycarbonyl derivative of the amino acid reacts with the compound containing a free amino group, the amino group of the amino acid is simultaneously freed of the aryloxycarbonyl group which was bonded thereto. Moreover, the removal of the aryloxycarbonyl group generates only relatively inoffensive by-products in the medium, which do not disrupt the synthesis. For example, when it is the phenyloxycarbonyl group, only phenol and carbon dioxide are generated. Consequently, when the compounds used contain very labile groups, such as certain protecting groups, the by-products generated in the medium do not bring about any degradation of these compounds. By comparison with the conventional synthesis routes, a synthetic peptide may be prepared by the process according to the invention in a much simpler manner. Thus, in order to prepare a dipeptide from two single amino acids having no reactive functions on their side chain, the process according to the invention only requires two simple steps, namely, in a first step, attaching an aryloxycarbonyl group to the amino group of the first amino acid and, in a second step, reacting according to the process of the invention the $N^\alpha$-aryloxycarbonylamino acid obtained with the second amino acid. The need for a step of activation of the carboxyl group of the first amino acid or for a coupling agent is superfluous, as is any deprotection step. The process according to the invention is consequently very particularly appropriate for the preparation of dipeptides.

The symbolic representations of the amino acids and of the peptides adopted in the description and the examples follow the IUPAC nomenclature recommendations generally adopted and which are described, for example, in "Nomenclature and Symbolism for Amino Acids and Peptides, Recommendations 1983", Eur. J. Biochem. (1984), 138, p. 9–37. Except where otherwise stipulated, all the amino acids described are (L)-amino acids.

The examples which follow illustrate the invention.

The various synthesis intermediates and products reported in the examples were characterized by various analytical methods, used under the following conditions:

optical rotation (α): measured at 589 nm at 25° C.

thin layer chromatography (TLC):
  MERCK 60F-254 silica gel plates
  eluents: Rf(1) ethyl acetate/n-butanol/acetic acid/water 1:1:1:1 Rf(2) acetonitrile/chloroform/acetic acid/water 5:2:2:1

HPLC chromatography:
  C-18 Vydac 5 µm column
  elution: gradient from 98% A+2% B to 25% A+75% B over 49 minutes (A=0.1% trifluoroacetic acid in water; B=0.1% trifluoroacetic acid in acetonitrile)
  flow rate=2 ml/min
  detection: UV 220 nm nuclear magnetic resonance (NMR):
  Brüker AMX 500 MHz machine
  shift data in ppm
  resonance responses: m=multiplet, s=singlet, d=doublet, t=triplet, q=quartet, quint=quintet, o=octet.

Example 1: Synthesis of tryptophyl-alanine and tryptophyl-(D)-alanine 2,922 g (9 mmol) of $N^\alpha$-phenyloxycarbonyltryptophan were dissolved in 20 ml of methanol. 3,204 g (36 mmol) of (D,L)-alanine were dissolved in 20 ml of water and converted to the triethylamine salt by addition of 3.643 g of the amine. The two solutions were mixed, followed by heating under gentle reflux, until the $N^\alpha$-phenyloxycarbonyltryptophan disappeared. The methanol was stripped off by evaporation under reduced pressure and the residue neutralized with 4.9 g (36 mmol) of $KHSO_4$ in 30 ml of water. After extraction of the majority of the phenol released during the reaction using ethyl acetate, the aqueous phase was diluted to 250 ml and then purified by preparative chromatography (DeltaPak C18 reverse phase). The pure fractions were combined and then freeze-dried to give 1.12 g of tryptophyl-alanine (Trp-Ala) and 0.66 g of tryptophyl-(D)-alanine (Trp-(D)-Ala), both optically pure. The products obtained have the following physicochemical properties:

Trp-Ala
$\alpha=+17.9$ (c=1, 1% acetic acid)
M.P.=104° C.
TLC: Rf(1)=0.63
HPLC Rt: 8.44 min
NMR ($^1$H) in DMSO-$d_6$ 10.92 (1H, s) NH indole, 8.45 (1H, broad s) NH Ala, 7.63 (1H, d) H4 indole, 7.32 (1H, d) H7 indole, 7.20 (1H, s) H2 indole, 7.05 (1H, t) H6 indole, 6.97 (1H, t) H5 indole, 4.16 (1H, broad q) H$\alpha$ Ala, 3.76 (1H, dd) H$\alpha$ Trp, 3.19 (1H, dd) H$\beta$A Trp, 2.90 (1H, dd) H$\beta$B Trp, 1.25 (1H, t) CH3 Ala Trp-(D)-Ala
$\alpha=+79.1$ (c=1, 1% acetic acid)
M.P.=107° C.
TLC: Rf(1)=0.59
HPLC Rt: 11.67 min
NMR ($^1$H) in DMSO-$d_6$ 10.88 (1H, s) NH indole, 8.20 (1H, broad s) NH Ala, 7.58 (1H, d) H4 indole, 7.32 (1H, d) H7 indole, 7.16 (1H, s) H2 indole, 7.05 (1H, t) H6 indole, 6.97 (1H, t) H5 indole, 4.05 (1H, broad q) H$\alpha$ Ala, 3.73 (1H, dd) H$\alpha$ Trp, 3.12 (1H, dd) H$\beta$A Trp, 2.88 (1H, dd) H$\beta$B Trp, 1.12 (1H, t) CH3 Ala

Example 2: Synthesis of ($\epsilon$-tert-butyloxycarbonyl)lysine ((Boc)Lys-(Boc)Lys)

1.46 g (4 mmol) of $N^\epsilon$-tert-butyloxycarbonyl-$N^\alpha$-phenyloxycarbonyl-lysine were dissolved in 16 ml of ethanol. 1.13 g (4.6 mmol) of $N^\epsilon$-tert-butyloxycarbonyllysine, 1.91 ml (13.8 mmol) of triethylamine and 4 ml of water were added thereto. The solution was heated under gentle reflux (≈80° C.) for 5 h and then cooled to room temperature and neutralized with 12.2 ml of 1N hydrochloric acid. The ethanol was removed by evaporation under vacuum. The residue (≈15 g) was placed in a refrigerator for 3 h. The precipitate formed was isolated by filtration and then washed with 7 ml of cold water and 25 ml of sulphuric ether. After drying, 1.42 g of (Boc)Lys-(Boc)Lys were obtained, corresponding to a yield of 75%. A sample recrystallized in a methanol/water mixture had the following physicochemical properties:

$\alpha=+19.2$ (c=1, methanol)
M.P.=180°–189° C.
TLC: Rf(1)=0.85
HPLC Rt: 20.79 min
NMR ($^1$H) in $CD_3OD$ 4.26 (1H, dd) H$\alpha$ Lys2, 3.86 (1H, t) H$\alpha$ Lys1, 3.04 (4H, quint) H$\epsilon$'s Lys1+2, 1.95 to 1.80 (3H, m) H$\beta$'s Lys, 1.73 (1H, m) H$\beta$ Lys, 1.50 to 1.40 (26H, m) H$\gamma$+$\delta$+t–Bu This example illustrates the very particular advantage of the process according to the invention for preparing homo-dipeptides, which may be obtained with a virtually stoichiometric molar ratio between the compound containing a free amino group and the $N^\alpha$-aryloxycarbonylamino acid.

Example 3: Synthesis of S-(trityl)cysteinamide ((Trt)CyS-$NH_2$)

48.5 g (100 mmol) of $N^\alpha$-phenyloxycarbonyl-S-tritylcysteine were dissolved in 200 ml of tetrahydrofuran. 135 ml of aqueous ammonia at a concentration of 25% (≈1.75 mol) were added thereto. This solution was heated for 5 h at 50° C. with stirring. After cooling, the reaction mixture was diluted with 400 ml of methyl tertbutyl ether. The aqueous phase obtained was discarded and the organic phase washed 3 times with 200 ml of an aqueous solution containing 5% of NaCl. It was subsequently treated with 50 ml of water and S-(trityl)cysteinamide was then precipitated in the form of a hemisulphate by addition of 13.6 g of $KHSO_4$ dissolved in 70 ml of water. It was isolated by filtration and washed with 150 ml of cold water and then dried. 29 g of product were obtained (yield: 71%). The product has the following physicochemical properties:

$\alpha=+18$ (c=1, methanol)
TLC: Rf(2)=0.80
HPLC Rt: 25.3 min
NMR ($^1$H) in $CD_3OD$ (+one drop of trifluoroacetic acid)

7.42 (6H, d), 7.32 (6H, t), 7.26 (3H, d) o- m- p-trityl, 3.53 (1H, t) H$\alpha$ 2.67 (2H, o) H$\beta$'s.

This example demonstrates that the process according to the invention may be used successfully to prepare the amide of an amino acid bearing, at the end of the side chain, a very labile protecting group.

We claim:

1. A process for the preparation of an $\alpha$-amino acid amide, comprising reacting a compound of formula $R_1R_2NH$ in which $R_1$ and $R_2$ independently represent hydrogen atoms, or alkyl, cycloalkyl, or aralkyl radicals, unsubstituted or substituted with at least one functional group containing at least one oxygen, nitrogen, or sulfur, in basic medium with an $\alpha$-amino acid containing an $N^\alpha$-aryloxcarbonyl group of formula R—O—CO—, in which R is an aryl group, linked to the nitrogen atom of an $\alpha$-amino group of said $\alpha$-amino acid, and isolating an amino acid amide free of said $N^\alpha$-aryloxycarbonyl group.

2. The process according to claim 1, wherein the aryloxycarbonyl group of said $N^\alpha$-aryloxycarbonyl contains 7 to 15 carbon atoms.

3. The process according to claim 2, wherein the aryloxycarbonyl group is a phenyloxycarbonyl or naphthyloxycarbonyl group, unsubstituted or substituted with at least one group chosen from alkyl groups containing 1 to 4 carbon atoms and nitro, halo and haloalkyl groups.

4. The process according to claim 3, wherein the aryloxycarbonyl group is a phenyloxycarbonyl, tolyloxycarbonyl, p-nitrophenyloxycarbonyl, 2,4-dinitrophenyloxycarbonyl, p-chlorophenyloxycarbonyl or p-trichloromethylphenyloxycarbonyl group.

5. The process according to claim 4, wherein the aryloxycarbonyl group is the phenyloxycarbonyl group.

6. The process according to claim 1, wherein the compound of formula $R_1R_2NH$ is selected from the group consisting of ammonia, primary or secondary amines, amino acids and peptides.

7. The process according to claim 6, wherein the compound is an amino acid.

8. The process according to claim 1, wherein said basic medium is an aqueous liquid medium containing a water-miscible organic solvent.

9. The process according to claim 1, wherein the $N^\alpha$-aryloxycarbonylamino acid is used at a concentration of 0.05 to 5 mol/l.

10. The process according to claim 1, wherein the molar ratio between the compound of formula $R_1R_2NH$ and the $N^\alpha$-aryloxycarbonylamino acid is at least equal to 1.

11. The process according to claim 6, wherein the compound is a peptide.

12. The process according to claim 7, wherein said amino acid is selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, glutamic acid and aspartic acid.

* * * * *